United States Patent [19]

Sites et al.

[11] Patent Number: 5,391,142
[45] Date of Patent: Feb. 21, 1995

[54] APPARATUS AND METHOD FOR THE EXTRACORPOREAL TREATMENT OF THE BLOOD OF A PATIENT HAVING A MEDICAL CONDITION

[75] Inventors: Jeffrey P. Sites, Plymouth; Wei Chen, St. Paul, both of Minn.

[73] Assignee: Organetics, Ltd., Coon Rapids, Minn.

[21] Appl. No.: 922,034

[22] Filed: Jul. 29, 1992

[51] Int. Cl.$^6$ .............................................. A61M 1/03
[52] U.S. Cl. .......................................... 604/4; 604/5
[58] Field of Search ................... 604/4, 5, 6, 19, 27, 604/28, 30, 31

[56] References Cited

U.S. PATENT DOCUMENTS

| | | |
|---|---|---|
| 3,881,483 | 5/1975 | Saussse . |
| 4,116,589 | 9/1978 | Rishton ............................. 604/4 X |
| 4,181,132 | 1/1980 | Parks . |
| 4,298,006 | 11/1981 | Parks . |
| 4,353,368 | 10/1982 | Slovak et al. ........................... 604/4 |
| 4,401,431 | 8/1987 | Arp . |
| 4,416,280 | 11/1983 | Carpenter et al. ................. 604/4 X |
| 4,466,804 | 8/1984 | Hino . |
| 4,476,867 | 10/1984 | Parks . |
| 4,479,798 | 10/1984 | Parks . |
| 4,540,399 | 9/1985 | Litze et al. .............................. 604/4 |
| 4,808,159 | 2/1989 | Wilson . |
| 5,074,838 | 12/1991 | Kroyer ................................... 604/4 |
| 5,104,373 | 9/1992 | Davidner et al. . |
| 5,186,713 | 2/1993 | Raible . |
| 5,270,005 | 12/1993 | Raible . |
| 5,277,820 | 1/1994 | Ash . |

Primary Examiner—Sam Rimell
Attorney, Agent, or Firm—Haugen and Nikolai

[57] ABSTRACT

Apparatus and a method for performing extracorporeal treatment of a patient's blood for various conditions. The apparatus includes means by which an extracorporeal blood circuit is defined. Such a blood flow circuit includes first means for cannulating a vein of a patient to define a blood egress point and second means for cannulating an artery of the patient to define a blood ingress point. A discontinuous conduit is provided to interconnect, in part, the first and second cannulating means. The apparatus also includes a module which includes a conduit portion. The module integrates a number of components into a single unit, and the conduit portion thereof is able to be interposed in the discontinuity in the discontinuous conduit to complete the blood flow circuit. The various components which are connected in the conduit portion include a pump, a device such as a heat exchanger to regulate the temperature of blood flowing through the conduit portion, and means for sensing the temperature, pressure, and flow rate of the blood passing through the conduit portion. In some applications, an oxygenator can also be included. A control console is provided to enable pressure and flow rate of the blood passing through the conduit portion to be controlled. Similarly, appropriate controls can be employed to regulate the temperature, and, when an oxygenator is included, a controller would, typically, be provided for the oxygenator also.

16 Claims, 4 Drawing Sheets

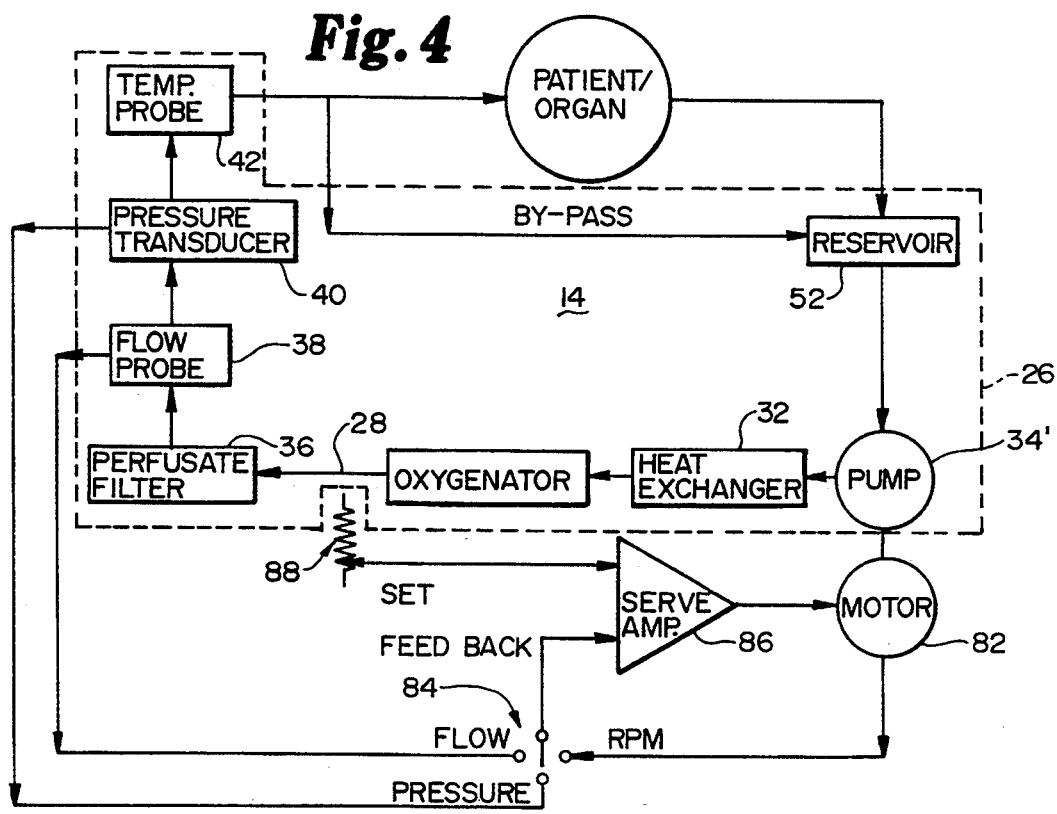
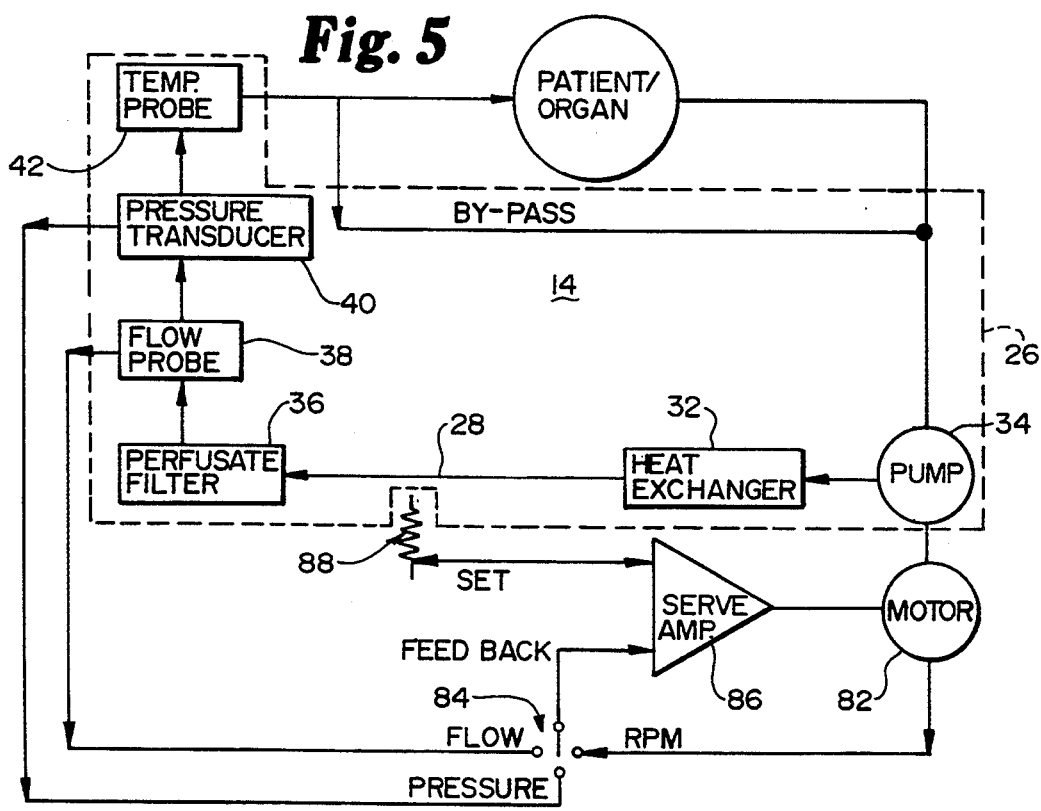

APPARATUS AND METHOD FOR THE EXTRACORPOREAL TREATMENT OF THE BLOOD OF A PATIENT HAVING A MEDICAL CONDITION

TECHNICAL FIELD

The present invention is related broadly to the field of medicine. More narrowly, however, the invention deals with the field of medical treatment devices and systems. The specific focus of the invention is the extracorporeal treatment of a patient's blood for one or more of various purposes. These can include extracorporeal membrane oxygenation for both infants and adult patients and hyperthermia treatment of a patient's blood to treat for cancer, acquired immune deficiency syndrome (AIDS), collagen vascular diseases such as rheumatoid arthritis and scleroderma, hepatitis, and Epstein-Barr virus.

BACKGROUND OF THE INVENTION

The twentieth century has seen great strides in the treatment and cure of various maladies. Diseases which once posed a threat to human life have veritably been eradicated.

Still, progress needs to be made in many areas. For example, numerous forms of cancer still plague the human race, and cures for various cancers elude medical science.

Even as cures are found for some diseases, new afflictions develop. For example, in the last decade, millions of people have been infected by the HIV virus and have died from resultant acquired immune deficiency syndrome (AIDS).

Various types of procedures have been postulated for use in the treatment of cancer and the HIV virus. One is hyperthermia. Hyperthermia is the controlled application of heat, either externally or extracorporeally. In extracorporeal hyperthermia, circulatory intervention is brought about, and blood of the patient is circulated external to the patient's body. Some sort of circulatory assist device is employed in extracorporeal hyperthermia.

Hyperthermia has been well-accepted as a cancer treatment, particularly for solid tumors. The technique of regional perfusion and hyperthermia to treat localized malignancies in the limbs has been explored both with and without chemotherapy. Hyperthermia without accompanying chemotherapy has been successful in treating refractory malignancies.

Kaposi's sarcoma is associated with limited life expectancy in HIV positive patients and, as statistics show, the incidence of HIV positive patients is growing geometrically. Evidence is available which demonstrates that hyperthermia, when applied to HIV positive patients with a circulatory support system being involved, can cause a reduction in symptoms and a reversal in the loss of lymphocytes.

In one study, circulatory support in combination with hyperthermia have been performed with in excess of fifty patients. Excellent results have been achieved. On-going studies have confirmed the success of such treatments.

Hyperthermia has been proposed as a valid method of treatment for other conditions also. These includes collagen vascular diseases such as rheumatoid arthritis and scleroderma, hepatitis, and Epstein-Barr virus.

Another procedure which, typically, involves circulatory intervention is one known as ECMO. The acronym stands for "extracorporeal membrane oxygenation". ECMO involves the use of cardiopulmonary bypass technology to effect circulatory and respiratory support for a patient's failing lungs. ECMO has been used in both newborns and adult patients. Indications which suggest the applicability of ECMO vary depending upon whether the patient is a newborn or adult. A newborn may be born with lungs that have been damaged (for example, by meconium aspiration or a birth defect). Damage resulting from such conditions can be repaired at great risk to the patient. Repair must, of course, be accomplished, since neither circumstance permits an infant to circulate oxygenated blood adequately. In the case of an adult patient, there has, typically, been a trauma giving rise to the need for ECMO treatment. Also, ECMO is frequently applicable as a means for treating a postoperative open heart surgery patient. Such patients are in severe distress with heart and lung failure.

Typically, when circulatory interventions are made, various non-integrated components are randomly assembled. Applicants are not aware of any fully-dedicated products which adequately integrate and coordinate operation of various assemblies and components for use in an extracorporeal treatment system for ECMO or hyperthermia.

The present invention is an apparatus and a method for use in performing ECMO procedures and hyperthermia treatments. The apparatus and method consolidate and coordinate components used in treatments. They, thereby, address many of the dictates and solve many of the problems of the prior art.

SUMMARY OF THE INVENTION

The present invention includes apparatus for use in performing hyperthermia treatment of a patient's blood. The components and sub-assemblies are consolidated and coordinated to facilitate implementation of use. The apparatus includes structures which define an extracorporeal blood flow circuit. Such a circuit includes a first cannula for use in cannulating a blood vessel of the patient. Such a cannula defines a blood egress point. A second cannula is used for cannulating a different blood vessel of the patient, and the second cannula defines a blood ingress point. A discontinuous conduit is provided to interconnect, in part, the first and second cannulae. A conduit portion of an integrated, sterile module has interposed therein a pump, a heat exchanger for regulating the temperature of blood flowing through the conduit portion, and sensors for ascertaining the temperature, pressure, and flow rate of blood passing through the conduit portion. The apparatus, further, employs a controller for regulating the pump and temperature regulating means in response to temperature, pressure, and blood flow rates sensed by the sensors.

In an embodiment of the apparatus invention for use in performing ECMO procedures, an oxygenator would be provided. The oxygenator would comprise part of the integrated, sterile module, and the oxygenator would, typically, be positioned in the conduit portion of the module.

Typically, a console would be employed with the module having various controls. Such controls would be used for selectively changing settings to achieve desired pressure and blood flow rate through the conduit portion.

If desired, the integrated, Sterile module could be a disposable component. As a result, a medical treatment facility could inhibit the possibility of contamination of the blood of one patient by HIV positive blood of a patient previously treated, and of health care workers involved in the treatment.

The invention also includes a method for treating a patient for a particular malady such as cancer or AIDS. The method includes a first step of cannulating the patient for extracorporeal blood circulation. In such a cannulating step, a blood flow circuit is defined between a first point of cannulation at a vein of the patient and a second point of cannulation at an artery of the patient. A patient's blood is then pumped through the circuit. As the blood passes through the circuit, it is heated to a first elevated temperature for a relatively short period of time. Thereafter, it is heated to a second elevated temperature, lower than the first elevated temperature, for a more extended period of time.

In a preferred embodiment of the method invention, the blood is heated to a first elevated temperature of between 42° C. to 48° C. The blood would, typically, be maintained at the first elevated temperature for a period of time of about one to two hours. Thereafter, the blood would be maintained at the second elevated temperature for a period of about two hours. The second elevated temperature, it is envisioned, would be between 37° C. to 39° C. The present invention is thus, an improved apparatus and method for performing extracorporeal treatment of a patient's blood. More specific features and advantages obtained in view of those features will become apparent with reference to the DETAILED DESCRIPTION OF THE INVENTION, appended claims, and accompanying drawing figures.

BRIEF DESCRIPTION OF THE DRAWINGS

FIG. 4 is a simplified diagram of the embodiment illustrated in FIG. 3; and

FIG. 5 is a simplified diagram of the embodiment illustrated in FIG. 2.

DETAILED DESCRIPTION OF THE INVENTION

Figure 2:
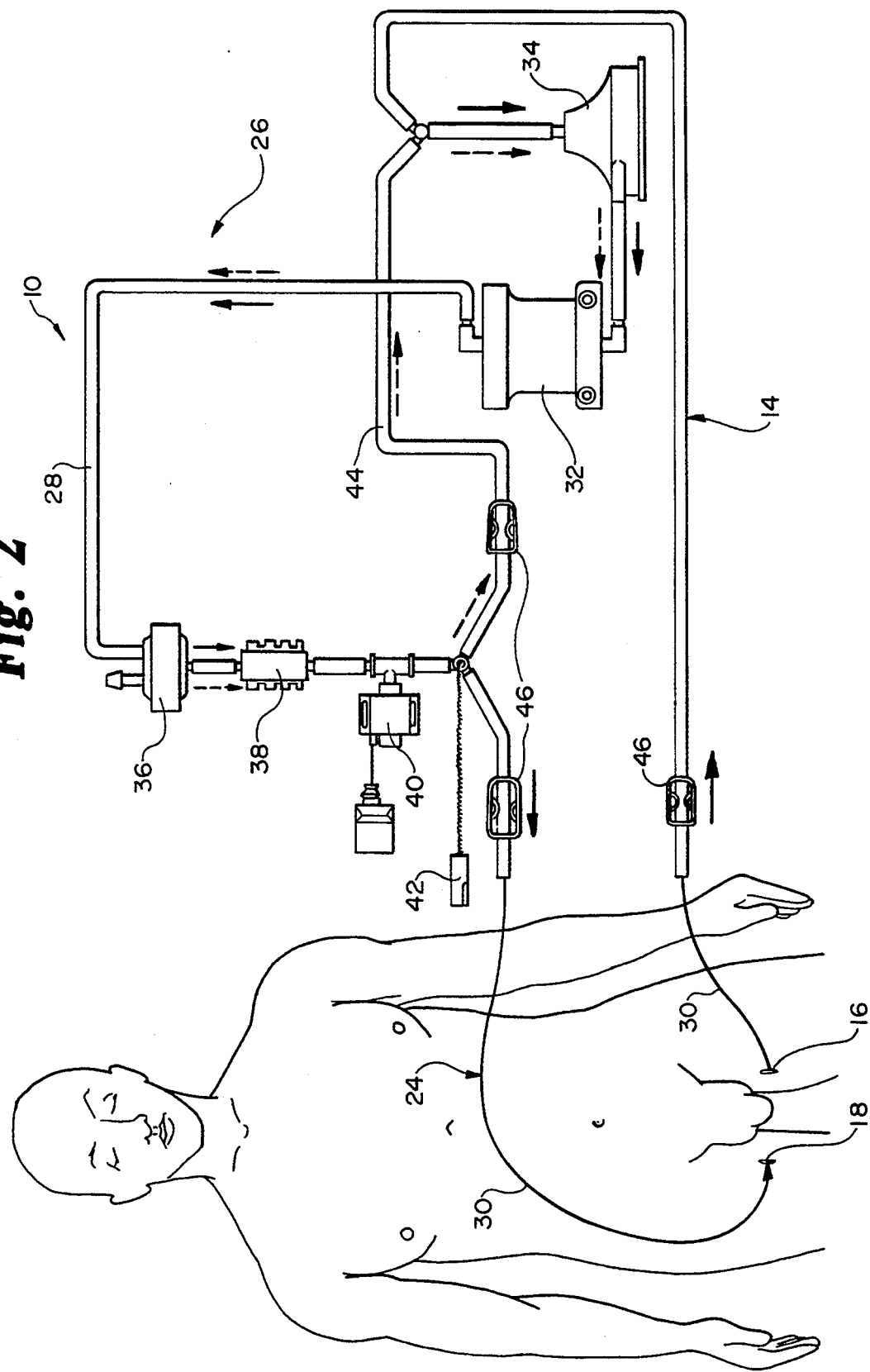
FIG. 2 is a mechanical diagram of one embodiment of the invention showing cannulation sites on a human adult.
Figure 3:
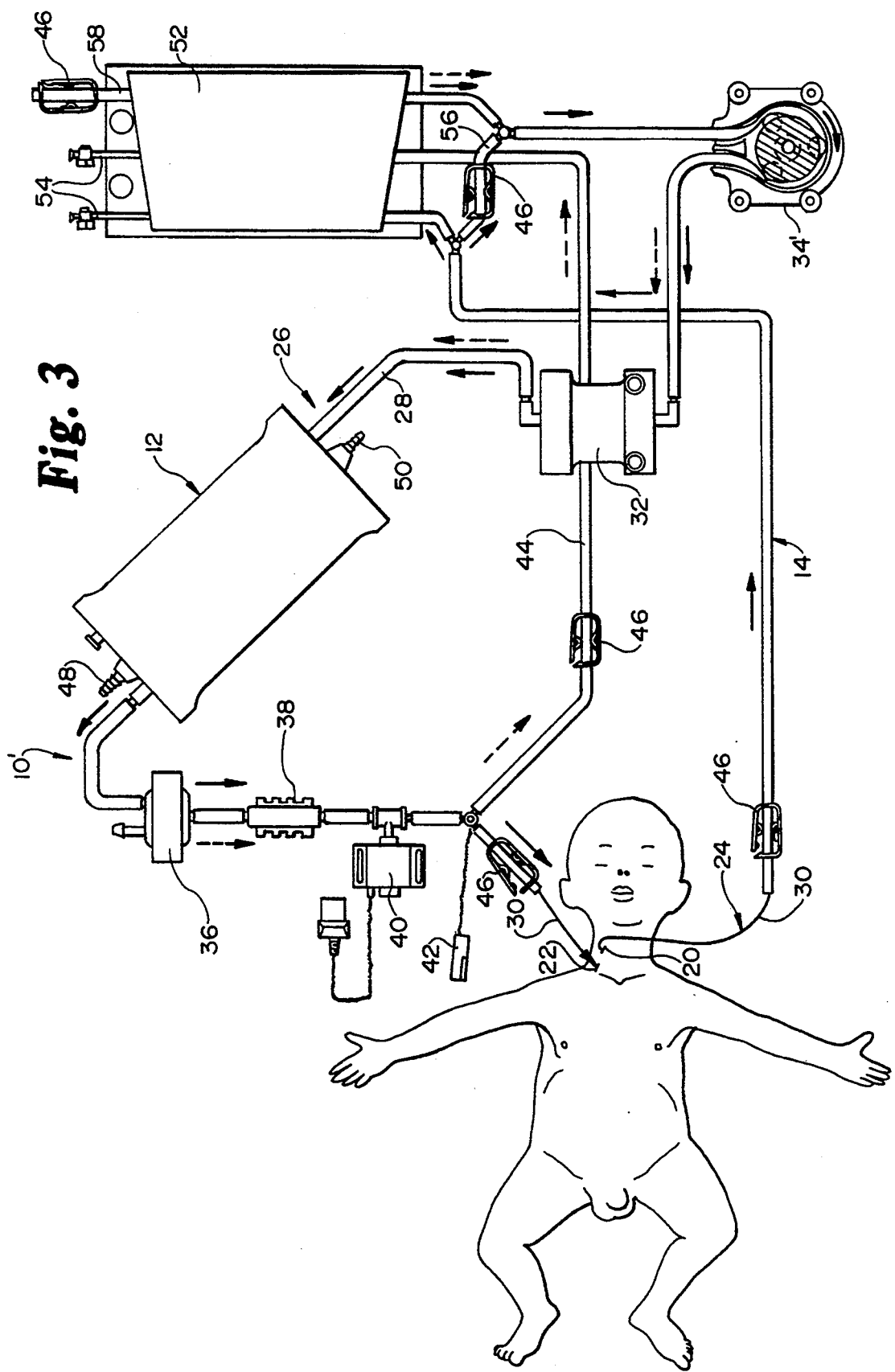
FIG. 3 is a mechanical diagram of a second embodiment of the invention and showing cannulation sites on a human infant.

Referring now to the drawings wherein like reference numerals denote like elements through the several views, FIG. 2 shows diagrammatically an apparatus 10 in accordance with the present invention for use in hyperthermia treatment of a patient's blood as a procedure for addressing a medical condition such as cancer, AIDS, collagen vascular diseases such as rheumatoid arthritis and scleroderma, hepatitis, and Epstein-Barr virus. FIG. 3 shows a similar diagram of an apparatus 10' in accordance with the present invention for administering .extracorporeal membrane oxygenation (ECMO) to a newborn infant. The embodiments of FIGS. 2 and 3 are quite similar with certain notable exceptions. Specifically, FIG. 3 illustrates a membrane oxygenator 12 interposed in a blood flow circuit 14 in addition to other components which will be described hereinafter.

Further, however, it will be noted that the locations of cannulation of the patients in the two figures are different. In the adult patient, a femoral vein in the left leg is cannulated as a point of egress of blood from the patient's body (as at 16), and a femoral artery in the patient's right leg is cannulated as a point of ingress of the blood back into the patient (as at 18). It will be understood that these two specific points of cannulation 16, 18 are not exclusive and that other cannulation locations are specifically contemplated. The locations illustrated in FIG. 2, however, have been found to be particularly appropriate, and ingress and egress points in different legs have been shown as being utilized so that a single leg of the patient is not compromised.

FIG. 3 illustrates cannulation of the patient at the jugular vein as at 20 (for blood egress) and at the cartoid artery as at 22 (for blood ingress). Again, these locations are not exclusive, but they have been chosen for illustrative purposes because they are more accessible than other locations and provide for safer access.

Figure 1:
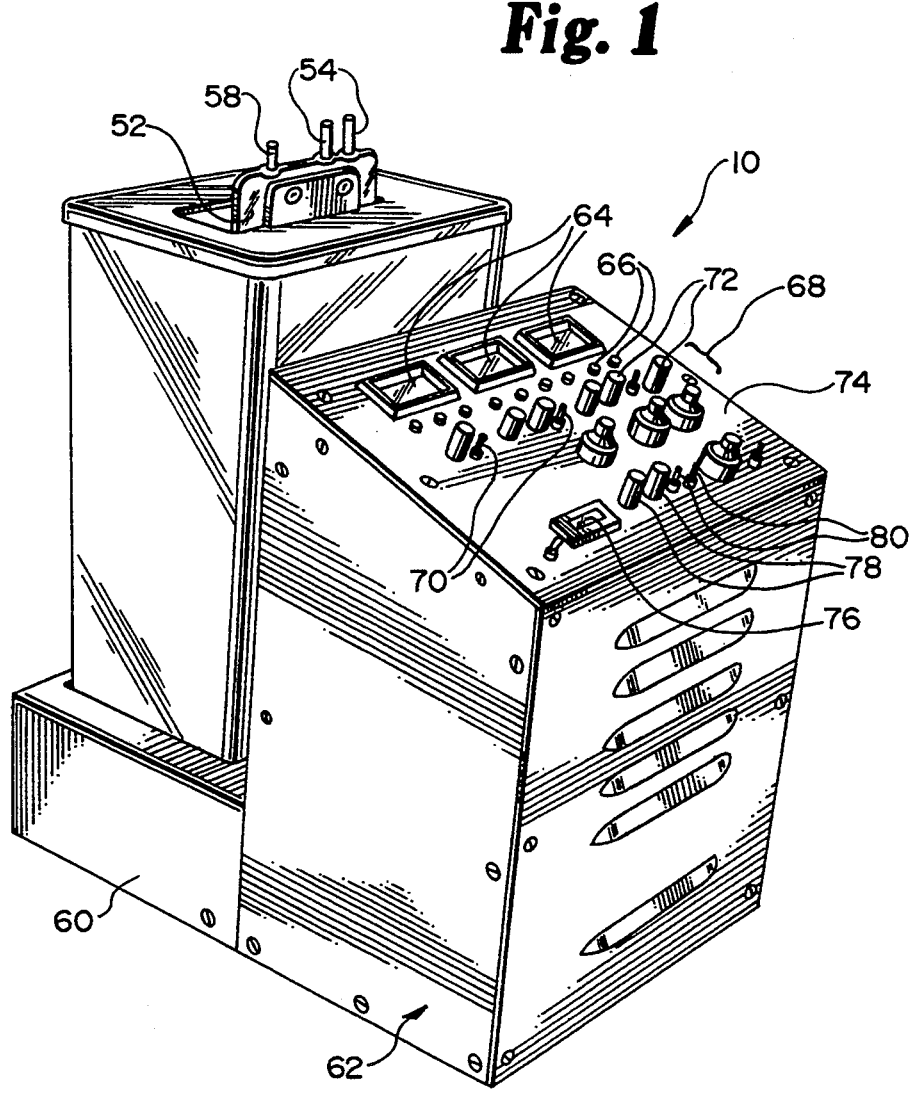
FIG. 1 is a simplified perspective view of the present apparatus invention.

FIG. 2 illustrates a series blood flow circuit 14 which includes first and second cannulae for cannulating the patient at a vein and artery, respectively, as previously discussed. A conduit 24 having a discontinuity therein is provided to interconnect, in part, the first and second cannulae. An integrated, sterile module 26, as best seen in FIG. 1, is interfaced with the discontinuity in the discontinuous conduit 24 to complete the series blood flow circuit 14. The module 26 contains all of the components which are exposed to blood in the course of a treatment. It includes a conduit portion 28 which is placed in communication with segments 30 of the discontinuous conduit 24 to complete the circuit 14.

The conduit portion 28 of the disposable module 26 has different components interposed therein. Blood is pumped from the egress point 16 of cannulation at a vein to a heat exchanger 32 by means of a pump 34 of appropriate construction. FIG. 2 illustrates a centrifugal pump 34, but it will be understood that this specific type of pump is not exclusive. In fact, in some embodiments, a centrifugal pump would be inappropriate.

FIG. 3 illustrates a positive displacement roller pump 34' functioning to circulate blood throughout the conduit portion 28 of the module 26 and back into the patient. Particularly in the case of infants, such a roller pump might be more appropriate. This type of pump would afford more positive control, and such control would be particularly desirable in the case of a newborn infant having a relatively short internal blood flow path.

FIG. 2 illustrates a heat exchanger 32 down-flow from the pump 34. The heat exchanger 32 would, particularly, in hyperthermia treatment systems, function to selectively elevate the temperature of the blood to a desired level.

The blood, after passing through the heat exchanger 32, passes through a perfusate filter 36. At this location, the perfusate can be purged of any impurities.

A flow probe or sensor 38 is shown as being in the series flow circuit 14 down-flow from the perfusate filter 36. The probe 38 serves to sense information with regard to the measure of flow rate of the perfusate passing through the circuit 14. FIG. 2 illustrates a pressure transducer 40 in the circuit 14 down-flow from the flow sensor 38. While it is important to know flow rate of the perfusate through the circuit 14, it is also important to know the pressure through the system also. Consequently, the patient being treated can be adequately protected.

FIG. 2 also illustrates a temperature sensor 42 in the circuit 14. The sensor 42, of course, serves to provide information with regard to the temperature of the blood flowing through the circuit 14.

FIG. 2 also shows a branch 44 of the circuit 14 which recirculates excess perfusate, not needed to be fed back into the patient, back to the pump 34 for recirculation. The recirculation branch 44 is also used during initial setup.

Also illustrated are a series of tubing clamps 46. Such clamps 46 serve, basically, as occluders which can be disposed to pinch tubing segments to preclude flow therethrough. In FIG. 2, three such tubing clamps 46 are illustrated. A first is immediately down-flow of the egress point on the patient. A second is located immediately prior to the location at which the blood reenters the patient's body. The third is positioned in the recirculation segment of the circuit 14.

As previously discussed, the system illustrated in FIG. 2 is intended primarily for hyperthermia treatment of a patient's blood. Typically, oxygenation and medicament delivery is not necessary. Consequently, no oxygenator is shown as being incorporated, and no means for delivering medicaments is shown either.

As also discussed hereinbefore, FIG. 3 illustrates different points of cannulation and the inclusion of an oxygenator 12. The oxygenator 12 is shown as having a gas inlet 48 through which gas can be introduced to maintain the blood at the desired level of oxygenation. Further, the oxygenator 12 has a gas outlet 50 for venting of unused gas.

Further, as previously discussed, FIG. 3 illustrates the employment of a positive displacement roller pump 34' rather than a centrifugal pump 34 as shown in FIG. 2. Finally, FIG. 3 illustrates a reservoir 52 for holding a volume of perfusate. The reservoir 52 receives perfusate both directly from the patient and from the recirculation branch 44 of the circuit 14 immediately prior to the perfusate reentering the patient's body. Optimum perfusate administration to the patient can be thereby regulated.

Further, however, the employment of a reservoir 52 can enable the administration of medicaments to the patient. Such medicaments can be introduced to the perfusate passing through the circuit 14 through tubes 54 entering the reservoir 52.

Finally, FIG. 3 shows two additional tube clamps 46. One of these tube clamps 46 is shown as being interposed in a bypass circuit portion 56 which bypasses the reservoir 52, and the second controls flow of air through a tube 58 through which air is evacuated from the reservoir 52.

In many respects, as will be able to be seen, the series flow relation circuit 14 shown in FIG. 3 is substantially the same as that in FIG. 2. That is, it includes a heat exchanger 32, a perfusate filter 36, a flow sensor 38, a pressure transducer 40 to facilitate measurement of pressure within the circuit 14, and a temperature sensor 42.

FIG. 1 illustrates, as previously discussed, an integrated, sterile module 26 in which are disposed all of the components described with reference to FIGS. 2 and 3 as being exposed to blood in the blood flow circuit 14. FIG. 1 also, however, illustrates a non-disposable base unit including a chassis 60 which removably mounts the integrated, sterile module 26. FIG. 1 further shows that the base unit includes a console or controller unit 62 for controlling operation of the hyperthermia or ECMO procedure being performed. The console 62 functions to regulate and maintain perfusate flow rate, pressure, and temperature at desired levels.

The console 62 is shown as having a series of digital display windows 64. Typically, such windows 64 would read temperature, pressure, and flow rate and display those parameters for both actual sensed values and inputted alarm range settings. Each display 64 can be provided with a series of visual alarms (i.e., LED's 66) for signaling when, for example, a desired range within which temperature, flow rate, or pressure, is intended to be maintained, is exceeded. A series of alarm setting controls 68 are also shown as being provided. Each window 64 has corresponding upper and lower range controls and an intermediately positioned toggle switch 70. The toggle switch 70 could be toggled between positions representative of upper and lower range settings. When in an upper range setting, for example, the appropriate dial 72 could be maneuvered to adjust the upper range limit.

Finally, the control panel 74 of the console 62 is shown as having a lower row of dials, displays, etc. These components can include a timer 76, rate and amplitude controls 78 for additional modes of operation (such as a pulsatile mode), an electronic filter 80 for filtering aberrant amplitude signals regarding, for example, pressure in the circuit 14, etc.

In the structure illustrated in FIG. 1, it is intended that the heater/cooler (not shown) for providing external fluid to the heat exchanger 32 would not comprise part of the console 62. Heat exchange would be implemented in a collateral manner known in the prior art.

While not specifically shown in FIG. 1, the console 62 contains therewithin a motor 82 which interfaces, through a wall, with the perfusate pump 34. This is done by providing the motor 82 with a magnetic rotor. As the motor 82 is driven, the rotor is caused to be rotated also. A magnetic element is provided in the pump 34, and such a magnetic element interfaces, through the wall, with the magnetic rotor. Driving of the rotor, in turn, translates to operation of the pump 34 to a desired level.

It will be understood that, when a positive displacement roller pump 34' is used rather than a centrifugal pump 34, the pump, substantially in its entirety, and its drive motor 82 could be positioned outside the integrated, sterile module 26. In such an embodiment, ends of segments of the conduit portion 28 within the module 26 would be mated with ports at the pump 34' external to the module 26.

FIGS. 4 and 5 illustrate schematically how the pump 34, 34' is controlled in each application in response to pressure and flow rate levels sensed by respective sensors 38, 40. Those figures show the integrated, sterile module 26 and the components typically enclosed therewithin by a dotted line.

In utilizing the present system for either hyperthermia or ECMO treatments, the patient is, as previously described, cannulated in the manner discussed. Initially, the patient is out of the circuit 14, and flow bypasses the patient. This is effected by manipulation of the appropriate tube clamps 46 to effect flow through the bypass branch circuit 44.

A selector switch 84 is manually positioned so that feedback will be provided from either the motor 82, the pressure transducer 40, or the flow probe 38. Input from the appropriate feedback component passes through the selector switch 84 to a servo-amplifier 86. The amplifier 86, in turn, inputs information to control the pump speed in an appropriate fashion to accomplish desired flow and pressure parameters.

FIGS. 4 and 5 also illustrate a variable resistor 88 which is manipulated in initiating the setting of a particular parameter. The parameter is set and, after the system is appropriately calibrated, the patient can be introduced into the flow system 14. Thereafter, continuous monitoring is performed of temperature, pressure, and flow rate. If the alarm system indicates that a parameter has gone outside the desired range, appropriate action can be taken to bring the parameter back within the range.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method for treating a patient for acquired immune deficiency syndrome (AIDS), comprising the steps of:
   (a) cannulating the patient for extracorporeal blood circulation wherein a blood flow circuit is defined between a first point of cannulation at a blood vessel of a patient and a second point of cannulation at a different blood vessel of the patient;
   (b) pumping the patient's blood through the circuit with a motor driven pump;
   (c) measuring the motor speed of said motor driven pump, the rate of flow of blood through the circuit and the fluid temperature and pressure within said circuit;
   (d) heating the patient's blood to a first elevated temperature for a relatively short period of time as it passes through the circuit;
   (e) subsequently heating the patient's blood to a second elevated temperature, lower than said first elevated temperature, for a more extended period of time as it passes through said flow circuit; and
   (f) adjusting the motor speed as a function of a deviation of one of current motor speed, said fluid pressure, said fluid temperature and said rate of flow from a desired set-point value.

2. A method in accordance with claim 1 wherein the patient's blood is heated to a first elevated temperature of between 42° C. to 48° C. for a period of about one to two hours.

3. A method in accordance with claim 2 wherein the patient's blood is heated to a second elevated temperature of between 37° C. to 39° C. for a period of about two hours.

4. A method in accordance with claim 3 wherein heating of the patient's blood to said first elevated temperature and to said second elevated temperature are sufficient to raise the temperature of the patient's bodily tissues to a temperature of above 37° C.

5. A method of performing hyperthermia treatment of a patient's blood to treat for various maladies, comprising the steps of:
   (a) cannulating the patient for extracorporeal blood circulation wherein a blood flow circuit is defined between a first point of cannulation of a blood vessel in a patient and a second point of cannulation of a different blood vessel a patient;
   (b) pumping the patient's blood through the circuit with a motor driven pump;
   (c) measuring the motor speed of said motor driven pump, the rate of flow of blood through the circuit and the fluid pressure and temperature within said circuit;
   (d) heating the patient's blood to a first elevated temperature for a relatively short period of time as it passes through the circuit;
   (e) subsequently maintaining the patient's blood at a second elevated temperature, lower than said first elevated temperature, for a more extended period of time as it passes through said flow circuit in order to elevate the temperature of the patient's bodily tissue above a normal level; and
   (f) adjusting the motor Speed as a function of a deviation of one of current motor speed, said fluid pressure, said fluid temperature and said rate of flow from a desired set-point value.

6. Blood treatment apparatus comprising in combination:
   (a) a base unit including
      (i) chassis-means for supporting one of a plurality of disposable modules, said chassis means including a console having operator adjustable controls and indicators thereon;
      (ii) a blood pump driver disposed in said console;
   (b) said disposable modules including:
      (i) a blood pump having an inlet and an outlet;
      (ii) heat exchanger means having an inlet and an outlet, said heat exchanger means inlet being coupled in circuit with said blood pump outlet for delivering heat energy to blood being pumped by said blood pump;
      (iii) a plurality of sensing probes coupled in a series flow relation circuit with said heat exchanger means outlet for sensing at least one of fluid pressure, blood flow rate and temperature of said blood flowing in said circuit; and
      (iv) means for coupling a patient's vascular system to said inlet of said blood pump and to said series flow relation circuit;
   (c) means for removably coupling said plurality of sensing probes to said indicators; and
   (d) means for coupling said operator adjustable controls and said blood pump to said blood pump driver.

7. The blood treatment apparatus and in claim 6 wherein said disposable modules further include blood oxygenating means in series flow relation circuit for introducing oxygen into the blood flowing through said circuit.

8. The blood treatment apparatus as in claim 6 wherein said disposable modules further include a bypass circuit for selectively shunting said means for coupling the patient's vascular system from said series flow relation circuit.

9. The blood treatment apparatus as in claim 7 wherein said disposable modules further include a bypass circuit for selectively shunting said means for coupling the patient's vascular system from said series flow relation circuit.

10. The blood treatment apparatus as in either claim 6 or claim 7 wherein said disposable modules further include a particulate filter in said series flow relation circuit.

11. The blood treatment apparatus as in claim 6 wherein said means for coupling a patient's vascular system includes means for cannulating first and second blood vessels of the patient.

12. The apparatus as in claim 11 wherein said blood vessels include two separate veins.

13. The apparatus as in claim 11 wherein said blood vessels include an artery and a vein.

14. The apparatus as in claim 6 and further including:
   (a) means for regulating the temperature of blood flowing in said series flow relation circuit; and
   (b) means for selectively controlling said blood pump and said temperature regulating means in response to temperature, pressure and blood flow rates sensed by said plurality of sensing probes.

15. A method for treating a patient for acquired immune deficiency syndrome (AIDS) comprising the steps of:
   (A) providing apparatus for subjecting the patient to hyperthermia, said apparatus including:
      (a) a base unit including
         (i) chassis means for supporting one of a plurality of disposable modules, said chassis means including a console having operator adjustable controls and indicators thereon;
         (ii) a blood pump driver disposed in said console;
      (b) disposable modules including
         (i) a blood pump having an inlet and an outlet;
         (ii) heat exchanger means having an inlet and an outlet, said heat exchanger means being coupled in circuit with said blood pump outlet for delivering heat energy to blood being pumped by said blood pump;
         (iii) a plurality of sensing probes coupled in a series flow relation circuit with said heat exchanger outlet for sensing at least one of fluid pressure, blood flow rate and temperature of said blood flowing in said circuit; and
         (iv) means for coupling a patient's vascular system to said inlet of said blood pump and to said series flow relation circuit;
      (c) means for removably coupling said plurality of sensing probes to said indicator; and
      (d) means for coupling said operator adjustable controls and said blood pump to said blood pump driver;
   (B) cannulating the patient's vascular system to create a blood egress point and a blood ingress point;
   (C) coupling said blood pump to said blood egress point and said series flow relation circuit to said blood ingress point;
   (D) driving said blood pump to circulate blood through said heat exchanger means while delivering heat energy to said heat exchanger for a time sufficient to elevate the patient's blood temperature to a point lethal to viruses in the blood; and
   (E) extracting heat energy from said heat exchanger to return the patient's blood temperature to a normal range.

16. A method of performing hyperthermia treatment of a patient's blood to treat for various maladies, comprising the steps of:
   (A) providing apparatus for subjecting the patient to hyperthermia, said apparatus including
      (a) a base unit having
         (i) chassis means for supporting one of a plurality of disposable modules, said chassis means including a console having operator adjustable controls and indicators thereon;
         (ii) a blood pump driver disposed in said console;
      (b) said disposable modules including
         (i) a blood pump having an inlet and an outlet;
         (ii) heat exchanger means having an inlet and an outlet, said heat exchanger means being in circuit with said pump outlet for delivering heat energy to blood being pumped by said blood pump;
         (iii) a plurality of sensing probes coupled in a series flow relation circuit with said heat exchanger outlet for sensing at least one of fluid pressure, blood flow rate and temperature of said blood flowing in said circuit;
         (iv) blood oxygenization means disposed in said series flow relation circuit for introducing oxygen into the blood traversing said circuit; and
         (v) means for coupling a patient's vascular system to said inlet of said blood pump and to said series flow relation circuit;
      (c) means for removably coupling said plurality of sensing probes to said indicators; and
      (d) means for coupling said operator adjustable controls and said blood pump to said blood pump driver;
   (B) cannulating the patient's vascular system to create a blood egress point and a blood ingress point;
   (C) coupling said blood pump to said blood egress point and said series flow relation circuit to said blood ingress point;
   (D) driving said blood pump to circulate blood through said heat exchanger means and said blood oxygenization means while delivering heat energy to said heat exchanger means for a time sufficient to elevate the patient's blood temperature to a point lethal to viruses in the blood; and
   (E) extracting heat energy from said heat exchanger to return the patient's blood temperature to a normal range.

* * * * *